(12) United States Patent
Urtsev et al.

(10) Patent No.: US 8,042,550 B2
(45) Date of Patent: Oct. 25, 2011

(54) SMOKE-SIMULATING PIPE

(76) Inventors: Vladimir Nikolaevich Urtsev, Magnitogorsk (RU); Dim Maratovich Khabibulin, Magnitogorsk (RU)

( * ) Notice: Subject to any disclaimer, the term of this patent is extended or adjusted under 35 U.S.C. 154(b) by 239 days.

(21) Appl. No.: 12/447,211

(22) PCT Filed: Aug. 30, 2006

(86) PCT No.: PCT/EA2007/000005
§ 371 (c)(1),
(2), (4) Date: Apr. 24, 2009

(87) PCT Pub. No.: WO2008/052570
PCT Pub. Date: May 8, 2008

(65) Prior Publication Data
US 2010/0006113 A1    Jan. 14, 2010

(30) Foreign Application Priority Data
Nov. 2, 2006 (RU) .................. 2006138666

(51) Int. Cl.
*A24F 1/22* (2006.01)
(52) U.S. Cl. ............. 131/194; 131/198.2; 131/270; 131/271; 131/273
(58) Field of Classification Search ............ 131/194, 131/198.2, 270–273
See application file for complete search history.

(56) References Cited

U.S. PATENT DOCUMENTS

| | | | |
|---|---|---|---|
| 4,184,496 A | | 1/1980 | Adair |
| 4,303,083 A | * | 12/1981 | Burruss, Jr. .......... 131/271 |
| 6,854,470 B1 | * | 2/2005 | Pu ....................... 131/273 |
| 7,726,320 B2 | * | 6/2010 | Robinson et al. ......... 131/200 |
| 2004/0003820 A1 | | 1/2004 | Iannuzzi |
| 2005/0211243 A1 | * | 9/2005 | Esser .................... 128/203.12 |
| 2005/0236006 A1 | * | 10/2005 | Cowan .................... 131/270 |
| 2006/0191546 A1 | * | 8/2006 | Takano et al. ............. 131/270 |

FOREIGN PATENT DOCUMENTS

| | | |
|---|---|---|
| DE | 30 42 937 | 5/1981 |
| DE | 30 42 937 A1 | 5/1981 |
| GB | 2 026 299 * | 2/1980 |
| JP | 06-114105 * | 4/1994 |
| RU | 2 067 876 C1 | 10/1996 |
| RU | 41 583 | 11/2004 |
| RU | 41583 U1 | 11/2004 |
| SU | 1528430 | 12/1989 |
| SU | 1528430 A1 | 12/1989 |

OTHER PUBLICATIONS

Online Mechanical English Translation, JP 06-114105, printed from the Internet on Feb. 9, 2011.*
English Abstract of RU 41583 U1.
Partial Translation of SU 1528430 A1.
Partial Translation of RU 2 067 876 C1.

* cited by examiner

*Primary Examiner* — Richard Crispino
*Assistant Examiner* — Dionne Walls Mayes
(74) *Attorney, Agent, or Firm* — Ladas & Parry LLP

(57) ABSTRACT

The invention is directed at the full simulation of a smoking process when a smoker uses the inventive pipe. Said smoking-simulating pipe comprises a shank (1) and a bowl (2) which are embodied in one piece, and a stem (4) which is detachable from the shank (1) and is provided with a bit, wherein a cavity (5), which is used for placing a sealed capsule (6) provided with a nicotine-containing or flavoring agent, is embodied in a smoking channel (14), and an electric heater (7) connected to a power supply (8), which is arranged in the walls of the bowl (2), is located before the capsule (6) in the smoking channel (14).

13 Claims, 8 Drawing Sheets

SMOKE-SIMULATING PIPE

FIELD OF THE INVENTION

The invention relates to medicine and medical technique and is used as means which is helpful in giving up smoking. It can be used under conditions when full smoking is impossible in, say, passenger compartments of airplanes or public places where smoking is prohibited. Besides, the claimed device permits satisfying a smoker's need of nicotine without a tobacco burning process and attendant isolation of smoke and combustion products which are health hazardous for the smoker and people around, such as CO, acetone, arsenic, henzpyrene, tars, to mention only few.

BACKGROUND OF THE INVENTION

Known is smoking-simulating means in a shape of a cigarette (US Patent Application 20040003820). The known means comprises a cylindrical body whose internal surface is covered by corrugated paper impregnated by a suitable aromatic substance reminding of the burning tobacco. The body accommodates a movable brush whose bristle scratches the corrugated paper thereby to promote isolation of an aroma.

The known device is disadvantageous in a weak simulation of a smoking process and inconvenient use. To obtain the fragrance of burning tobacco, a brush is moved inside a body all the time, with a brush handle coming out via a filter in the "smoker's" mouth. Besides, the user inhales only the smell of the burning tobacco, whilst for the full simulation of a smoking process it is necessary to provide at least a minimum introduction of nicotine into an organism whose absence is likely to create certain psychological and/or physiological inconveniences.

Known is smoking-simulating means in a shape of a plastic stem connected with a cylindrical body thru which the user can inhale an air flow (RU 2067876). The body accommodates a cavity for placing a sealed capsule therein (cartridge) comprising a porous polymer material soaked with a nicotine containing agent which can be represented by liquid nicotine or a mixture of nicotine, menthol and ethanol. The body is provided with means for capsule seal failure.

The known device is disadvantageous in the weak simulation of a smoking process, more exactly, in absence of light and sound effects accompanying the smoking process.

A most pertinent prior art solution to the claimed matter as to technical essence is a smoking-simulating device, as shown and described in patent U.S. Pat. No. 6,854,470. The device is in a shape of a cigarette, more exactly, has a hollow cylindrical body, with a filter arranged in one of its end portions and an electrical bulb in another, connected to a power supply arranged within the body. Various flavouring blends are placed before filter means thru which air is passed the user inhales. Besides, located in the body magnets, a conductive element and an integrated circuit module for the acoustic reproduction (musical accompaniment) of the "smoking" process.

The known device is disadvantageous in that it does not allow simulating a smoking process using a pipe, inasmuch as it is known that smokers are divided into categories using for smoking: a) cigarettes, b) cigars, c) pipes. Such being the case, the known technical solution that is a very close simulation of the cigarette smoking process cannot satisfy the smokers who are used to smoking a pipe.

The claimed technical solution is directed at the full simulation of a smoking process with the use of a pipe by the smoker.

SUMMARY OF THE INVENTION

Said result is attained owing to the fact that a smoking-simulating pipe comprises a shank and a bowl which are embodied in one piece, and a stem with a bit, which is detachable from the shank, with the provision of, between the shank and the stem in a smoking channel, a cavity which is used for placing a sealed capsule with a nicotine-containing or flavouring agent and an electric heater is located before the capsule in the smoking channel, which heater is connected to a power supply which is arranged in the walls of the bowl.

Said result is achieved owing to the fact that a cavity for placing a capsule is provided with means for its seal failure.

Said result is attained owing to the fact that a capsule is embodied in the form of a hermetically sealed cylinder whose base parts are closed with membranes.

Said result is attained owing to the fact that a power supply is located in a cavity provided in the bottom part of a bowl.

Said result is achieved owing to the fact that a power supply is located in a cavity provided in the top part of a bowl.

Said result is attained owing to the fact that a power supply is provided with a push-button switch situated on the surface of a bowl.

Said result is achieved owing to the fact that a power supply is provided with a current intensity regulator.

Said result is attained owing to the fact that a current intensity regulator is configured and designed as a ring-shaped rheostat provided at the detachment of a shank and a stem.

Said result is achieved owing to the fact that on the external surface of a stem bit are arranged sensors which allow switching on a current supply source at the moment of contact thereof.

Said result is attained owing to the fact that the top portion of a pipe bowl is rotatable and combined with a mode selector switch.

Said result is achieved owing to the fact that in a smoking channel between a bowl and a capsule is provided a sensor which allows switching on a current supply source at the moment of air passage air via the channel.

Said result is attained owing to the fact that it is provided with a sound source.

Said result is attained owing to the fact that a sound source is embodied as an acoustic transducer connected to a current supply source.

Said result is attained owing to the fact that a sound source is arranged within a bowl.

Said result is attained owing to the fact that a sound source is in a shape of one or more through bores of variable section whose inlets and outlets are positioned on the internal surface of a bowl.

Said result is achieved owing to the fact that it is provided with a light source located inside a bowl and connected to a current supply source.

Said result is attained owing to the fact a light source is embodied as a Ne tube securely fastened within a bowl to follow the perimeter thereof.

Implementation of a smoking-simulating pipe as one piece in a shape of a shank with a bowl and a stem with a mouth engaging portion which is detachable from the shank would afford the fullest simulation of the pipe used by the smoker. Execution of a cavity between the shank and the stem in a smoking channel to accommodate a sealed capsule with a nicotine-containing or flavouring agent allows one to reject combustion of tobacco filling said pipe bowl during a full smoking process and to substitute it with the vapours of agents contained in said sealed capsule. Arrangement of an electric heater before the capsule in the smoking channel, which is connected to a power supply positioned in the walls of the bowl allows for heating the vapours of the nicotine-containing or flavouring agent being admitted to the smoker, thus simulating the smoking process in the fullest manner. Arrangement of the power supply in the walls of the bowl is most convenient because of its relatively large overall dimensions and relatively large dimensions of the walls which just make possible arrangement of said current supply sources therein.

Providing a pipe cavity for a capsule to be placed, with means for its seal failure allows the smoker to open a nicotine-containing or flavouring agent source for its use at a determined moment.

A nicotine-containing or flavouring agent capsule can most advantageously be used in the form of a sealed cylinder whose base parts are closed with membranes.

Considering the fact that a pipe bowl has thick walls and a bottom part, it is advantageous to place a power supply for feeding an electric heater in the bottom part of the bowl or in the top part thereof.

For the operation of a heater to be provided for a suitable time, it is necessary to fit a power supply with a switch to be most preferably represented by a push-button switch situated on the side surface of a bowl or a bottom part thereof.

In some cases, depending on a particular agent usable in a capsule or on a subjective perception by a smoker, of simulation of a smoking process, a power supply is desired to be provided with a current intensity regulator which allows to a different degree of intensification, for heating vapours at the exit of the stem of a pipe.

Said current intensity regulator can be selected from among those known and arranged in any one of the portions of a pipe, albeit it is most convenient to implement the current intensity regulator in the form of a circular rheostat situated at the detachment of a shank and a stem.

For the fullest simulation of a smoking process, on the external surface of a stem bit are arranged sensors for switching on a power supply upon contact therewith, which factor permits in particular cases of realization to optimize simulation of a smoking process owing to the fact that the power supply for heating the vapours of an agent being admitted to the smoker thru the stem will be connected at times when the stem is between the smoker's lips.

In particular cases of realization, the top part of a pipe bowl is rotatable and combined with a mode selector switch, which permits to further optimize a smoking-simulating process due to the selection by the smoker, of various operating conditions of the pipe which are most suitable to him at a given moment.

To further optimize a smoking-simulating process and to provide an efficient performance of a power source, in a smoking channel between a bowl and a capsule is situated a sensor for the connection of the power supply at the moment of passage of air via the channel.

For a fuller smoking-simulating process, a pipe is fit with a sound source in a shape of, for example, an acoustic transducer connected to a power supply and is arranged within a bowl or in the form of one or more through bores of variable section whose inlets and outlets are positioned on the internal surface of the bowl.

More, for a further simulation of a smoking process, a pipe is fitted with a light source situated within a bowl and connected to a power supply. And inasmuch as during the smoking process, the smoker does not see the interior of the bowl but only its rim, it is most preferable to implement the light source in the form of a Ne tube fixed inside the bowl to follow the perimeter thereof.

A concept of the invention, as being claimed and as set forth in the application, will now be described in detail with reference to the drawings.

DESCRIPTION OF THE PREFERRED EMBODIMENT OF THE INVENTION

Figure 1:
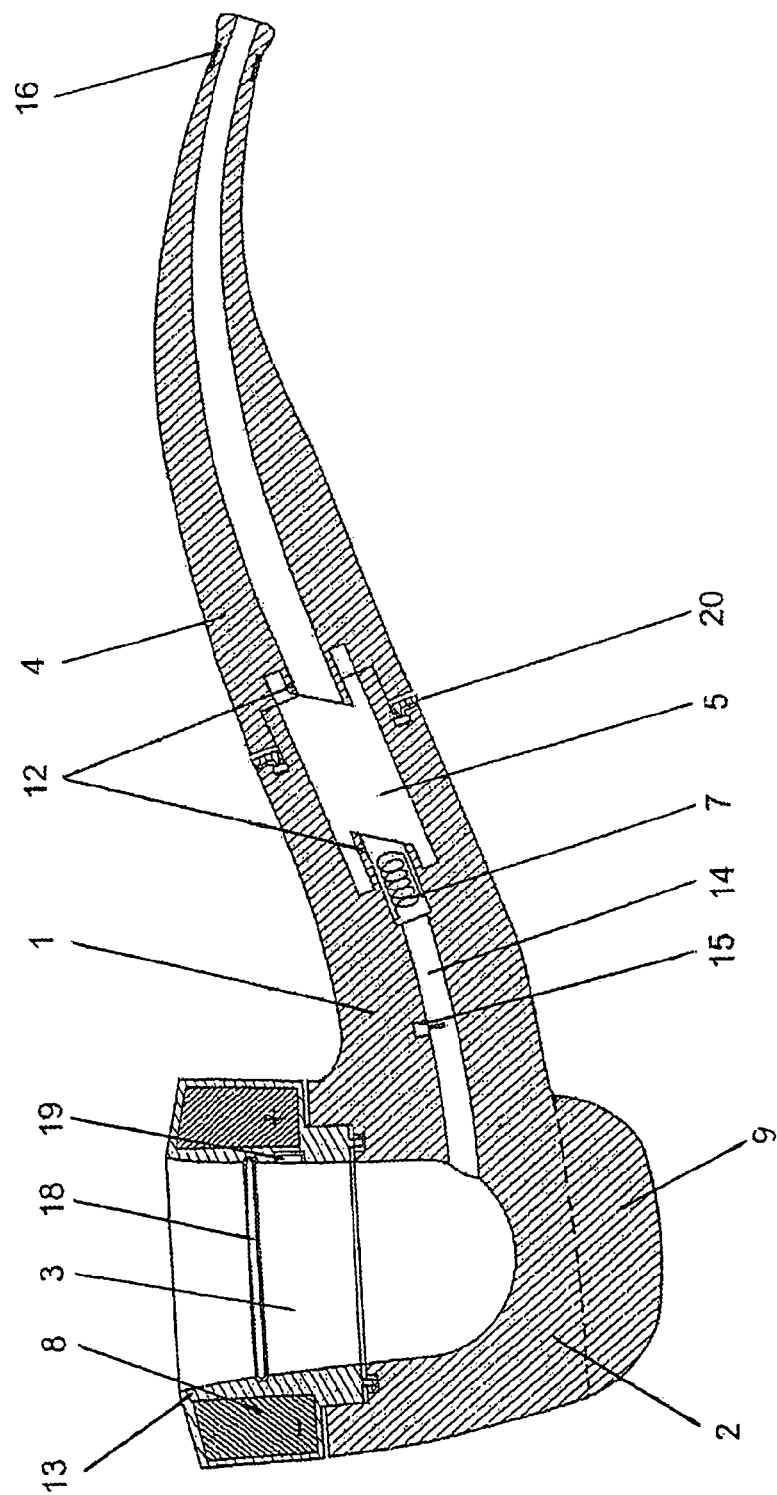
FIG. 1 illustrates the longitudinal section of the alternative embodiment of a pipe without providing it with a capsule with a nicotine-containing or flavouring agent.
Figure 2:
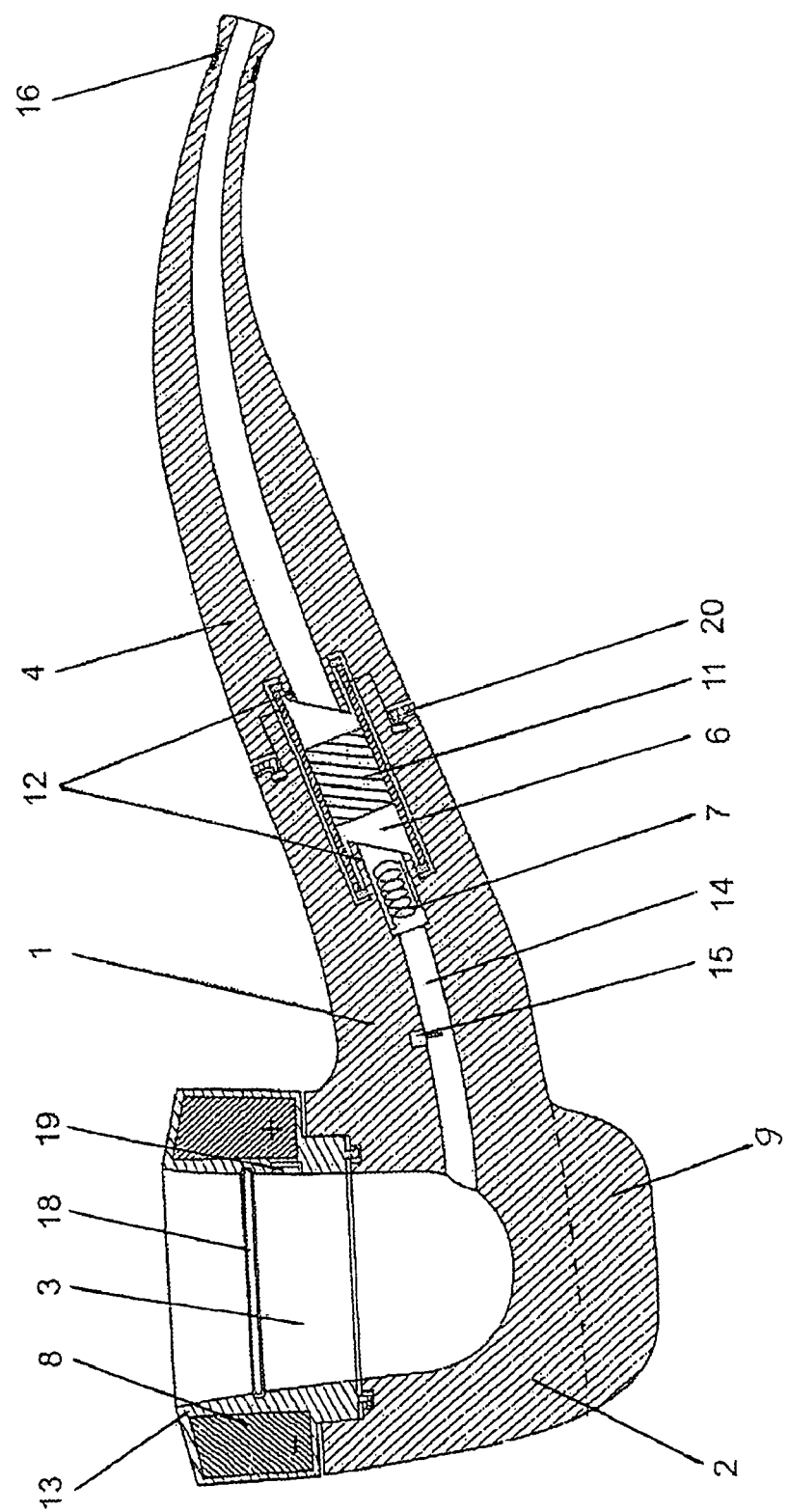
FIG. 2—longitudinal section of the alternative embodiment of a pipe provided with a capsule with a nicotine-containing or flavouring agent.
Figure 3:
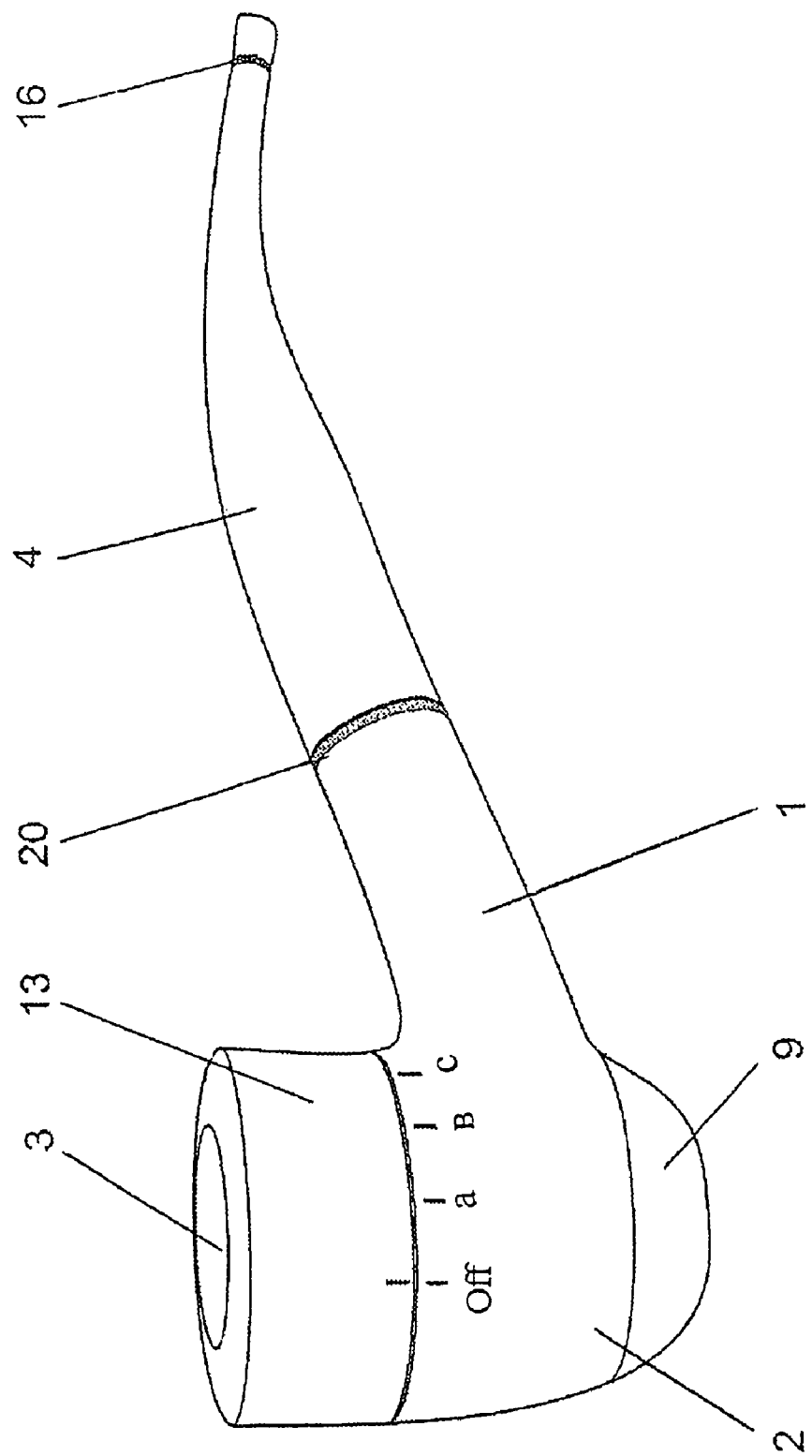
FIGS. 3 and 4—pipe from lateral sides thereof, general views.
Figure 4:
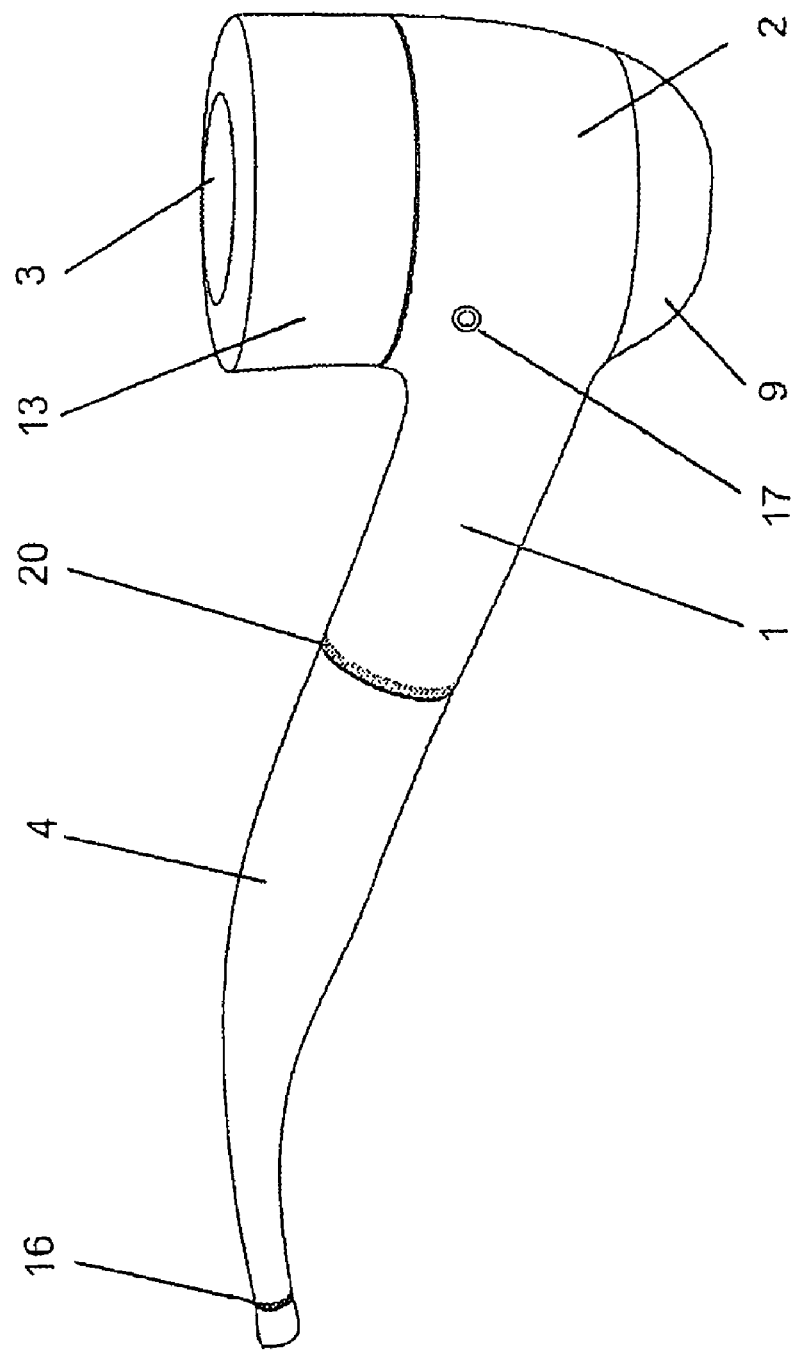
Figure 5:
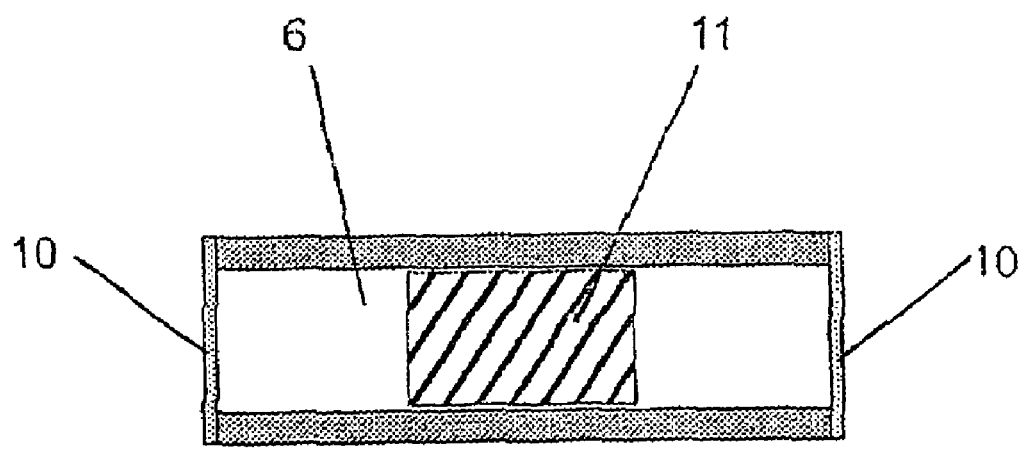
FIG. 5—longitudinal section of a capsule with a nicotine-containing of flavouring agent.
Figure 6:
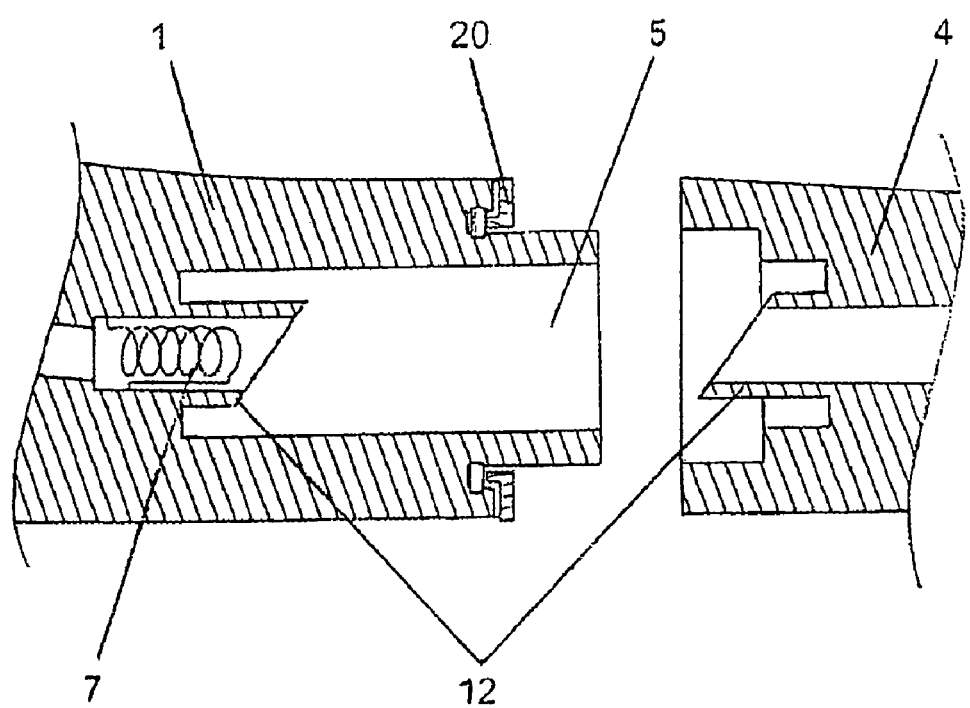
FIGS. 6-8—successive phases of arrangement of a capsule within a pipe and its seal failure.
Figure 7:
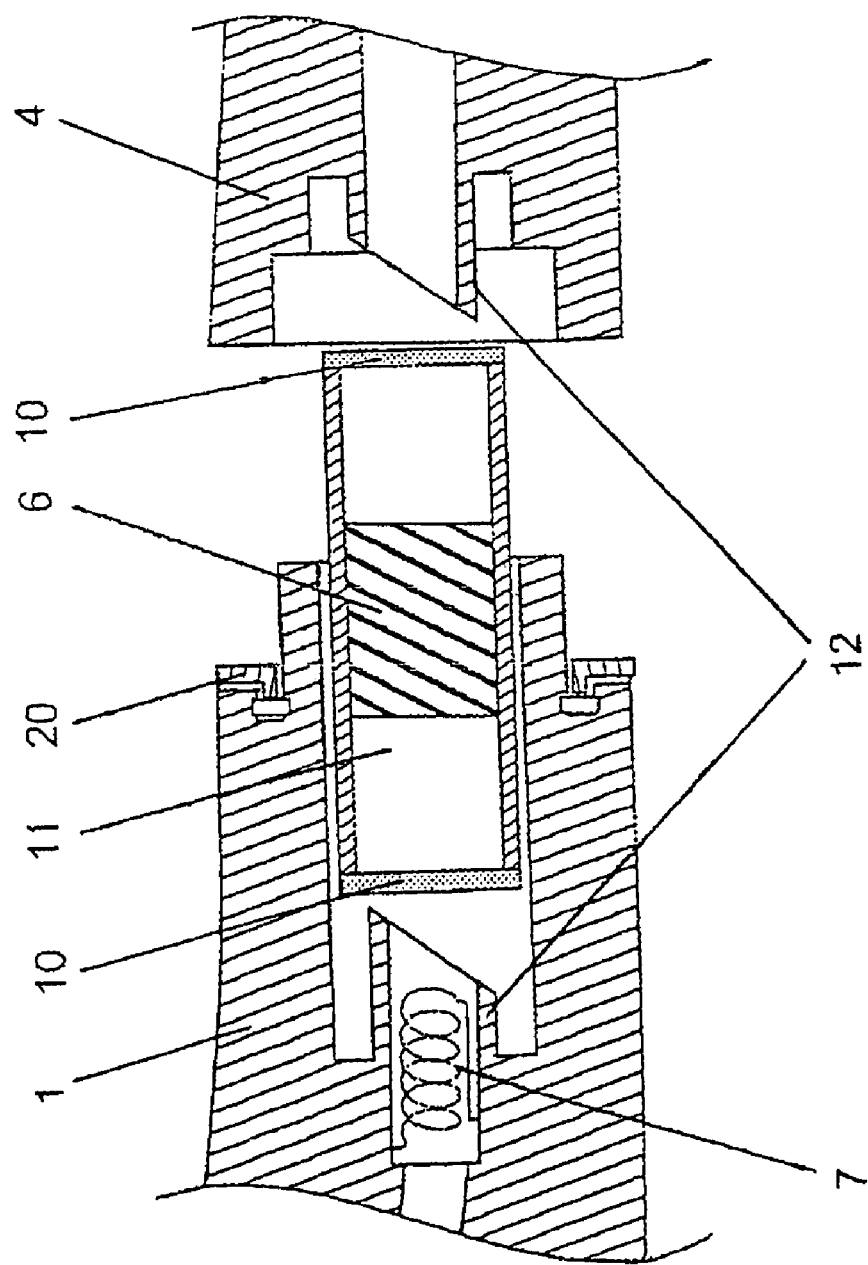
Figure 8:
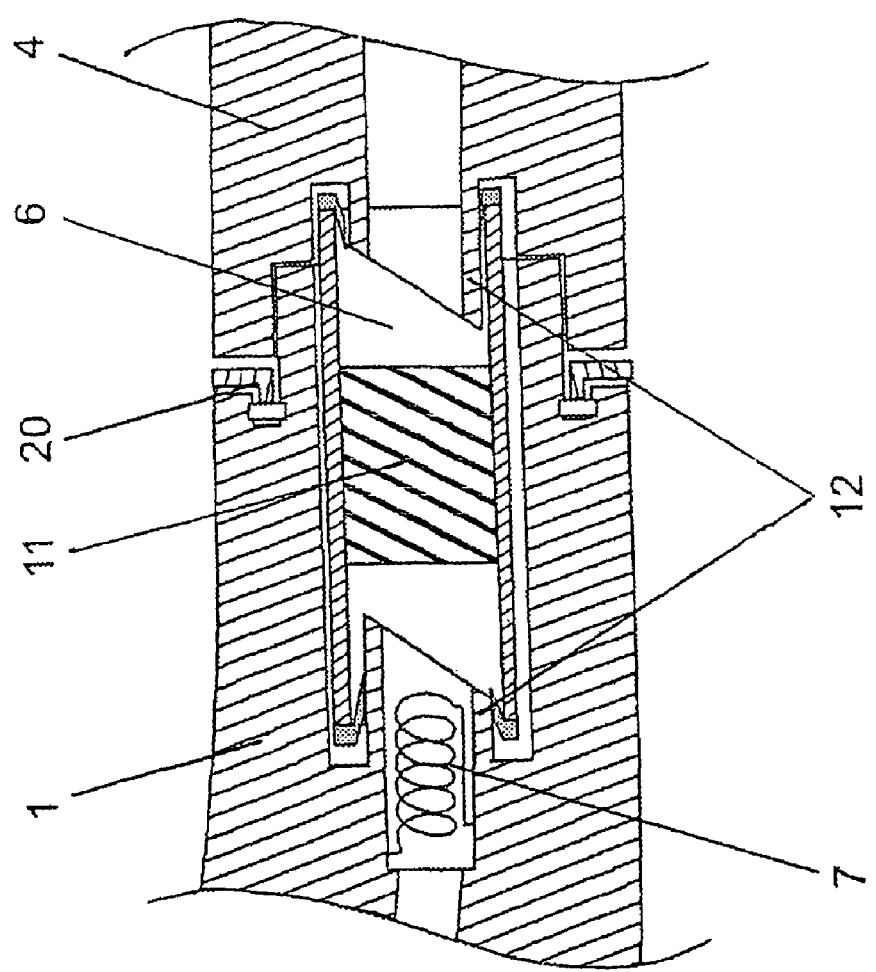

In the most preferable variant of realization, a pipe comprises a shank 1 with a bowl 2 embodied in one pieces in which is provided a cavity 3 that is not closed and a stem 4 being detachable from the shank 1, a cavity 5 is provided between the shank 1 and the stem 4 to accommodate a sealed capsule 6 with a nicotine-containing or flavouring agent and an electric heater 7 is arranged before the cavity 5 and connected to a power supply 8 arranged in a detachable bottom part 9 of the bowl 2 or a rotatable top part 13 of the bowl 2. The capsule 6 is in a shape of a hollow cylinder. Sealing of the capsule 6 is provided by membranes 10 situated on end portions. Inside the capsule 6 is placed a porous material 11 containing nicotine or a flavouring agent. The cavity for accommodating the cavity 5 is provided with means for its seal failure 12.

The top part 13 of the bowl 2 is rotatable. On rotation of the top part 13 of the bowl 2, the switch mode of a pipe takes place.

A channel 14 accommodates a sensor 15 for switching on the power supply 8 during air motion in the channel 14. On the external surface of the mouthpiece of the stem 4 there is a sensor 16 for connection of the power supply 8 upon contact with the sensor 16. On the bowl 2 is arranged a push-button switch 17, with the power supply 8 connected on pressing same. The cavity 3 (not closed) accommodates a light source 18 and a sound source 19. The heating intensity of the electric heater 7 is regulated by a circular rheostat 20 disposed at the detachment of the shank 1 and the stem 4.

Provision is made of four operating conditions of a pipe. If the rotatable top part 13 of the bowl 2 is set in the OFF position, the power supply 8 is disconnected.

While switching the rotatable top part 13 of the bowl 2 in the "a" position, the electric heater 7, the light source 18 and the sound source 19 are connected and work if the sensor 16 is contacted .

While switching the rotatable top part 13 of the bowl 2 in the "b" position, the electric heater 7, the light source 18 and the sound source 19 are connected and work if air moves in the channel 14 and movement is fixed by the air movement sensor 15.

While switching the rotatable top part 13 of the bowl 2 in the <<c>> position, the electric heater 7, the light source 18 and the sound source 19 are connected and operate if the push-button switch 17 is pressed.

A pipe is used in the following manner. The stem 4 is detached from the shank 1 and the capsule 6 is placed in the cavity 5. Furthermore, the stem 4 is connected with the shank 1, with seal failure of the capsule 6 proceeding during this process which has been due to rupture of the membranes 10 by the seal failure means 12.

Furthermore, the user selects pipe performance being most suitable to him. In the case of "a" performance, upon contact of the mouthpiece of the pipe with the smoker's lips, the electric heater 7, the light source 18 and the sound source 19 are connected. The user pulls in air via the channel 14, which is heated in the electric heater 7 and is saturated with nicotine or flavouring agent vapours while passing thru the capsule 6. The light source 18 and the sound source 19 produce an effect of tobacco burning in the pipe cavity 3 that is not closed.

In the case of "b" performance, at the time of sucking in air by the user thru the channel 14, which is fixed by the air movement sensor 15, the electric heater 7, the light source 18 and the sound source 19 are connected. The user pulls in air via the channel 14, which is heated in the electric heater 7 and is saturated with nicotine or flavouring agent vapours while passing thru the capsule 6. The light source 18 and the sound source 19 produce an effect of tobacco burning in the cavity 3 that is not closed.

In the case of "c" performance, the user himself switches on the electric heater 7, the light source 18 and the sound source 19 by way of pressing the push-button switch 17.

The pipe allows one to adequately simulate a smoking process by heating air and also due to characteristic light and sound effects.

What is claimed is:

1. A smoking-simulating pipe comprising a shank and a bowl which are embodied in one piece and a stem which is detachable from the shank and is provided with a bit, a cavity is provided between the shank and the stem in a smoking channel to arrange a sealed capsule with a nicotine-containing or flavouring agent, and an electric heater is situated before the capsule in the smoking channel and connected with a power supply accommodated in the walls of the bowl wherein:
    the power supply is provided with a push-button switch arranged on the surface of the bowl;
    on the external surface of the stem bit are arranged sensors for connection of the power supply upon contact therewith;
    in the smoking channel between the bowl and the capsule is positioned a sensor for connection of the power supply at times of air passage via the channel;
    and wherein the top part of the bowl of the pipe is rotatable and combined with a mode selector switch.
2. The pipe according to claim 1, wherein the cavity for placing the capsule is fitted with means for its seal failure.
3. The pipe according to claim 1, wherein the capsule is in a shape of a hermetically sealed cylinder whose base parts are closed by membranes.
4. The pipe according to claim 1, wherein the power supply is situated in a cavity provided in a bottom part of the bowl.
5. The pipe according to claim 1, wherein the power supply is arranged in a cavity provided in a top part of the bowl.
6. The pipe according to claim 1, wherein the power supply is provided with a current intensity regulator.
7. The pipe according to claim 6, wherein the current intensity regulator is executed in the form of a circular rheostat situated at the detachment of the shank and the stem.
8. The pipe according to claim 1, wherein it is provided with a sound source.
9. The pipe according to claim 8, wherein the sound source is in a shape of an acoustic transducer connected to the power supply.
10. The pipe according to claim 9, wherein the sound supply is accommodated inside the bowl.
11. The pipe according to claim 8, wherein the sound source is implemented in the form of one or more through bores of variable section whose inlets and outlets are positioned on the internal surface of the bowl.
12. The pipe according to claim 1, wherein it is fitted with a light source situated inside the bowl and connected to the power supply.
13. The pipe according to claim 12, wherein the light source is executed in the form of a Ne tube securely fastened within the bowl to follow the perimeter thereof.

* * * * *